United States Patent [19]

Cummings et al.

[11] Patent Number: 4,650,646

[45] Date of Patent: Mar. 17, 1987

[54] METHOD FOR REDUCING CONDENSATE ON STERILIZED GOODS

[75] Inventors: Arthur L. Cummings, Erie; David A. Karle, McKean; William R. Miller, Erie, all of Pa.

[73] Assignee: American Sterilizer Company, Erie, Pa.

[21] Appl. No.: 684,623

[22] Filed: Dec. 21, 1984

[51] Int. Cl.⁴ .............................................. A61L 2/08
[52] U.S. Cl. ...................................... 422/26; 422/30; 34/39; 44/3 R
[58] Field of Search ................ 423/555; 106/118, 310; 252/194; 44/3 C, 3 R, 3 B, 3 A, 3 D; 422/26, 27, 37, 39, 30, 292; 34/39; 126/263; 426/407, 408, 511, 521

[56] References Cited

U.S. PATENT DOCUMENTS

| 3,314,413 | 4/1967 | Cambridge | 44/3 R |
| 4,238,447 | 12/1980 | Wolff | 422/26 |
| 4,338,098 | 7/1982 | Yamaji | 44/3 C |
| 4,372,916 | 2/1983 | Chamberlain et al. | 422/26 |
| 4,501,259 | 2/1985 | Apellaniz | 44/3 R |

*Primary Examiner*—David L. Lacey
*Attorney, Agent, or Firm*—Robert D. Yeager; Christine R. Ethridge

[57] ABSTRACT

An improvement in a process for sterilizing goods comprising a method for substantially reducing condensate on the processed goods. The method includes producing an exothermic reaction during the process between effective amounts of at least two reactants to release at least a sufficient quantity of heat proximate the goods to substantially reduce condensate on the goods at the conclusion of the process. Hydratable salts may be housed in a liner which is permeable to a condensate vapor present in the process. Contact between the vapor, or condensate, and the salt produces the exothermic reaction during the process.

6 Claims, 1 Drawing Figure

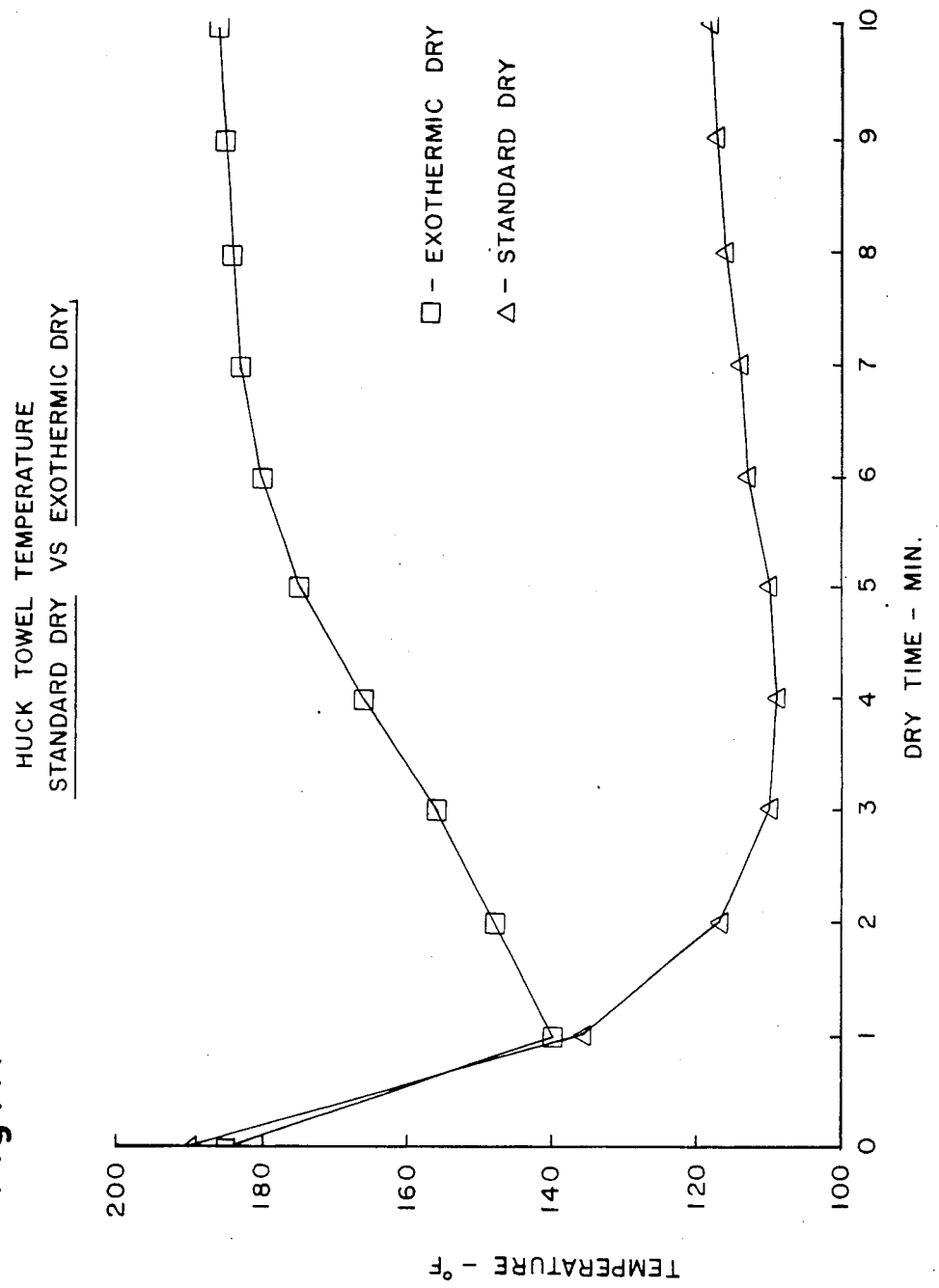

METHOD FOR REDUCING CONDENSATE ON STERILIZED GOODS

BACKGROUND OF THE INVENTION

1. Field of the Invention

The present invention relates to methods and means for reducing condensate on sterilized goods, and more particularly, to such methods and devices utilizing exothermic reactions.

2. Description of the Prior Art

When medical instruments, such as surgical instruments are sterilized, they are generally placed in an instrument tray on a huck towel. The tray is then wrapped in muslin or a synthetic wrap. Alternatively, the instruments may be placed in a specially adapted sterilization container which is permeable to the sterilizing agent. In those sterilization processes in which condensable vapors, such as steam, are present, a problem often encountered with such packaged goods is "wet pack", the collection of condensate in the package or on the goods. Condensate may also collect in hard to dry areas of hard goods, whether packaged or unpackaged.

Moisture remaining on the goods at the conclusion of the sterilization process is unacceptable. Accordingly, there is a need for a method or a means to reduce the condensate on such sterilized goods. There is a further need for such a method or means which is easy and inexpensive to use and which will not interfere with the sterilization process.

SUMMARY OF THE INVENTION

The present invention provides both a method and a means for easily and inexpensively reducing condensate on sterilized goods. In a process for sterilizing goods in which a portion of the goods may be enclosed in a sterilant-permeable package, and during which process a condensable vapor contacts the goods, a method of yielding substantially dry goods at the conclusion of the process includes the step of producing an exothermic reaction during the process between effective amounts of at least two reactants to release at least a sufficient quantity of heat proximate the goods to substantially reduce condensate on the goods at the conclusion of the process.

The method may include producing the exothermic reaction at a predetermined stage of the process. The method may also include releasing a predetermined quantity of heat. The quantity of heat may be sufficient to substantially reduce the formation of condensate on the goods. The release of such a quantity of heat to reduce condensate formation is preferably initiated before the condensate formation begins. Where the goods are held in a tray or are themselves made of a material, such as a metal which will retain heat, the exothermic reaction releases heat to the material which in turn will retain the heat throughout the process to substantially reduce the formation of condensate proximate the material. Reduction of condensate occurs by reducing the amount of condensate formed during the heating process and by reducing the differential temperature between initial and final temperatures. The temperature of the goods is raised by the exothermic reaction so that less steam heat is required to raise the goods to the predetermined sterilizer temperature.

Alternatively, the quantity of heat released may be sufficient to reevaporate condensate which formed on the goods. The release of such quantity of heat to reevaporate the condensate is preferably initiated after the condensate formation.

The quantity of heat released can be controlled by the amount of the reactants employed and their properties, specifically the heat and rate of reaction.

One or more reactants may be housed in a liner which is adapted to release the heat produced by the exothermic reaction. The liner may include a barrier separating the reactants. The barrier is preferably adapted to permit contact between the reactants at a predetermined stage in the process to produce the exothermic reaction.

In one embodiment of the method of the present invention, the reactants may be the condensable vapor and a hydratable salt, such as calcium sulfate, sodium borate, sodium acetate or calcium chloride, having a heat of hydration sufficient to release the desired quantity of heat. Preferably, the hydratable salt has a drying temperature greater than the maximum temperature of the sterilization process.

BRIEF DESCRIPTION OF THE DRAWING

FIG. 1 is a graph comparing the temperatures over time of the interior of a standard tray to a tray wherein the preferred embodiment of the method of the present invention was practiced.

DETAILED DESCRIPTION OF THE PREFERRED EMBODIMENT

The method of the present invention is applicable to any process during which condensation may occur and heat is required to heat or dry the goods subjected to the process. The method is particularly applicable to sterilization processes during which a condensable vapor contacts the goods to be sterilized. For purposes of describing a preferred embodiment of the method, the condensable vapor will be steam and the process will be steam sterilization. It should be understood, however, that the method can be adapted for use in other sterilization processes during which moisture is present and it is desirable to yield dry goods at the conclusion of the process.

Heat from a source other than the process steam is used to heat the goods, or the package enclosing the goods, to prevent condensate formation or to reevaporate condensate already formed.

The method utilizes the heat released during an exothermic reaction between effective amounts of two reactants. Preferably, the reactants are water, either in the form of steam or liquid condensate, and a hydratable salt. Water is plentiful in a steam sterilizer. Utilizing it to correct the wet pack problem provides both simplicity and savings.

The salt incorporates water into its crystal structure and forms a chemical bond with the water molecules. The heat released upon the formation of the bond is the heat of hydration. There are several suitable hydratable salts commercially available.

A suitable salt for the method may be chosen by examining the properties of a particular substance. For purposes of the method of the present invention, the salt should have the following desirable properties:

TABLE I

DESIRED CHARACTERISTICS OF CHEMICAL SUBSTANCES

| PROPERTY | DESIRED CHARACTERISTIC |
| --- | --- |
| Heat of Hydration | high |
| Hydration Rate | fast |

TABLE I-continued

| DESIRED CHARACTERISTICS OF CHEMICAL SUBSTANCES | |
|---|---|
| PROPERTY | DESIRED CHARACTERISTIC |
| Density | low |
| Heat Capacity | low |
| Melting Point | >sterilizer temperature |
| Thermal Conductivity | moderate to high |
| Hydration Volume Change | moderate |
| Drying Temperature | >sterilizer temperature |
| Cost per Calorie | low |
| Deliquescence | preferably none |
| Hydration Site Density | high |

Although the above listed properties are relevant to the choice of an optimum hydratable salt, the essential property is the heat of hydration. A sufficient quantity of heat must be released during the exothermic reaction to reduce the condensate on the instruments at the end of the process.

The melting point is preferably greater than the sterilizer temperature, generally 132° C. (270° F.), to avoid the necessity of packaging the salt. However, in one embodiment of a means for practicing the method of the present invention, the melting reactants may be packaged. Nonmelting reactants may also be packaged. The package must be adapted to permit sufficient heat to escape to reduce the condensate on the goods, but must retain the melted or nonmelted reactants. If the reactants are the steam and a hydratable salt, the package must be permeable to the steam. The package must be made of a material which can withstand sterilizer conditions. If the reactants are other substances, they may be separated by a barrier which is adapted to melt at a predetermined temperature achieved at a desirable stage during the process to initiate the exothermic reaction. The barrier may be a distinct structure which physically separates the reactants, such as a plastic material adapted to melt at a predetermined temperature. Alternatively, the barrier may be the physical nature of the reactants themselves.

For example, the reactants may be crystalline in nature and may melt upon reaching the desired temperature. The melted reactants flow together to effect the exothermic reaction. The reactants may be viscous substances which become less viscous at the desired temperature and run together to effect the reaction. In another embodiment, one or more reactants may be a deliquescent substance and one or more may be crystalline. When the predetermined temperature is achieved the deliquescent reactant dissolves and is absorbed by and reacts with the crystalline reactant.

In any event, it may be desirable to package the reactant for ease of handling. For example, a pad or liner containing a hydratable salt may be wrapped with the instruments, in a layer of the towel, or may be placed beneath the towel in the sterilization tray. Such a pad may be inserted into hard to dry portions of hard goods. The pad or liner can be disposable or a reusable accessory.

Alternatively, loose reactant may be pulverized and dispersed evenly over the sterilization tray, in the folds of the towel or in, on, or adjacent to the instruments or other goods.

The drying temperature is preferably greater than the maximum sterilization temperature to avoid the release of the water from the salt during the process.

Those skilled in the art will recognize that a suitable hydratable salt, based on the above listed criteria, can be readily selected by comparing the properties of a variety of such salts in any of the available handbooks of physical properties of chemical compounds.

For example, the properties of several common hydratable salts are compared below:

TABLE II

| PHYSICAL PROPERTIES OF SOME COMMON HYDRATABLE SALTS | | | | | |
|---|---|---|---|---|---|
| FORMULA | DENSITY g/cc | MELTING POINT °C. | DEHYDRATION TEMP., °C. | SPEC. HT. cal/gdeg | HEAT OF FUSION cal/g |
| $CaSO_4$ | 2.96 | 1450 | — | — | — |
| $CaSO_4.\frac{1}{2}H_2O$ | — | — | 163 | — | — |
| $CaSO_4.2H_2O$ | 2.32 | — | 128 | 0.265 | — |
| $CaCl_2$ | 2.15 | 772 | — | 0.164 | — |
| $CaCl_2.2H_2O$ | 0.83 | — | 200 | — | — |
| $CaCl_2.6H_2O$ | 1.68 | 30 | 200 | 0.320(s) | 41 |
| $AlCl_3$ | 2.44 | 190 (bp 183) | — | 0.188 | — |
| $AlCl_3.6H_2O$ | — | (100, decompose) | — | 0.313(s) | — |
| $NaC_2H_3O_2$ | 1.53 | 324 | — | 0.339 | — |
| $NaC_2H_3O_2.3H_2O$ | 1.45 | 58 | 120 | 0.344(s) 0.846(l) | (~50) |
| $MgCl_2$ | 2.32 | 712 | — | — | — |
| $MgCl_2.6H_2O$ | 1.56 | (118, decompose) | — | — | 40 |
| $FeCl_3$ | 2.80 | 282 | — | — | — |
| $FeCl_3.6H_2O$ | — | 37 | >280 | — | 54 |
| $Na_2B_4O_7$ | 2.37 | 741 | — | 0.234 | — |
| $Na_2B_4O_7.10H_2O$ | 1.73 | 75 | 200 | 0.385(s) | (~50) |

Calcium sulfate, $CaSO_4$, sodium acetate, $NaC_2H_3O_2$ and sodium borate, $Na_2B_4O_7$ appear to be suitable hydratable salts for use in the method of the present invention. Each of these substances has a melting point greater than the maximum sterilization temperature. Calcium chloride, $CaCl_2$, in its fully hydrated state has an unacceptable melting point. Aluminum chloride, $AlCl_3$, and magnesium chloride, $MgCl_2$, decompose in their hydrated forms below the maximum sterilization temperature, and are thus, unsuitable. Ferric chloride, $FeCl_3$ has a dehydration temperature which is too great and thus, will not lose waters of hydration at a reasonable drying temperature.

Table III compares the critical properties for purposes of the exothermic reaction of the present method. The "hydration heat" is the amount of heat released per gram of dry salt during the formation of the indicated hydrate. The hydration heats reveal that for every gram of water taken up by one of these salts, about 4 kcal of heat is released. In contrast, only about 0.5 kcal is required to vaporize a gram of water.

The "heat consumed" per gram of dry salt is required to heat the hydrated salt from room temperature to a typical sterilization temperature (132° C.). The "net heat available" is the difference between the hydration heat and the heat consumed. "Hydration Expansion" is the ratio of specific volumes of the hydrated to dry salt.

The last two columns in Table III are included to illustrate the relative amounts of dry reactant salts which might be required to accomplish two approximate heat demands: (1) 100 kcal to heat an entire typical 52×26.3 cm tray and its contents, and (2) 6 kcal to vaporize the largest typical amount of water (about 10 grams) in a wet pack. For illustrative purposes, the material requirement is given in terms of the minimum depth of the salt reactant, assuming such reactant is dispersed evenly and continuously (no air gaps) over the complete 1367 cm² bottom of a sterilization tray, and assuming that moisture hydrates all the available salt to the indicated degree. The depth can be calculated by dividing the heating requirement (100 or 6 kcal) by the product of the net heat available, the density of the dry salt and the area of the bottom of the sterilization tray. For example, the depth of calcium sulfate required to release 100 kcal, assuming complete hydration to 2 moles water per mole of CaSO$_4$, is calculated as follows:

$$D = \frac{H}{(n.h.a.)(\rho)(A)} = \frac{100,000 \text{ cal.}}{(1014 \text{ cal/g}) \cdot (2.96 \text{ g/cm}^3) \cdot (1367 \text{ cm}^2)} = .024 \text{ cm}$$

where
D is the depth of reactant required;
H is the heat requirement;
n.h.a. is net heat available taken from Table III;
$\rho$ is the density of the dry salt; and
A is the area of the tray bottom.

necessary to vaporize the water typically found in wet packs.

The exothermic reaction and its associated liberation of heat begins as soon as the moisture contacts the hydratable salt and continues until all of the salt is hydrated. The heat radiates in all directions but will concentrate in the package, tray or goods proximate to the salt.

The rate at which heat will be released is determined by (1) the rate of the hydration reaction characteristic of a particular reactant, and (2) the rate at which steam or condensate contacts the dry salt. The pore size of the package in which the goods are enclosed and the grain size of the salt contribute to the rate of steam contact. Generally, the greater the surface area of salt available, the faster the rate.

Referring to Table III above, it can be seen that the relative change in volume upon hydration is often large. However, if the salt is evenly dispersed over the relevant area, a two or threefold increase in volume for such small amounts of reactant is an insignificant factor.

Calcium sulfate was evaluated. A single layer of the hydratable salt was dispersed over the bottom of a 10½×20½ in. instrument tray. The tray was then exposed to a sterilization process during which the maximum temperature achieved was 270° F. A twenty minute drying phase followed. Temperature monitors were placed on the tray. The monitors demonstrated that an exothermic reaction occurred during the drying stage. It is reasonable to assume that the reaction occurred throughout the sterilization process. At the conclusion of the process the tray was completely dry. FIG. 1 illustrates the temperature differential between a tray without the hydratable salts (Δ) and a tray with the salts (□). Measurements were taken from the Huck Towel. The standard tray produced wet goods. The exothermic tray produced dry goods.

Calcium sulfate, and other salts having high melting points, can be recycled by drying the hydrated salt in an oven after each use.

The reactant employed in the exothermic reaction is preferably nontoxic and noncorrosive and should be stable under the particular sterilization conditions. If the reactant is enclosed in a pad or liner, however, the

TABLE III

| | | AVAILABLE HEAT AND MATERIAL NEEDS | | | | NEEDS for 1367 cm² tray for | |
|---|---|---|---|---|---|---|---|
| SYSTEM | | HYDRATION HEAT cal/g | HEAT CONSUMED cal/g | NET HEAT AVAILABLE cal/g | HYDRATION EXPANSION Vhyd/ | 100 Kcal depth | 6 Kcal depth |
| dry | Hydration | dry | dry | dry | Vdry | cm | cm |
| CaSO$_4$ | .½H$_2$O | 264 | ~30 | ~235 | 1.4 | 0.105 | 0.006 |
| CaSO$_4$ | .2H$_2$O | 1050 | 36 | 1014 | 1.6 | 0.024 | 0.002 |
| CaCl$_2$ | .2H$_2$O | 1306 | ~164 | 1142 | 3.4 | 0.030 | 0.002 |
| CaCl$_2$ | .6H$_2$O | 3901 | 244 | 3657 | 2.5 | 0.009 | 0.005 |
| NaC$_2$H$_3$O$_2$ | .3H$_2$O | 2608 | 206 | 2402 | 1.8 | 0.020 | 0.001 |
| Na$_2$B$_4$O$_7$ | .10H$_2$O | 3572 | 199 | 3373 | 2.6 | 0.009 | 0.0005 |

It can be seen that theoretically, very small amounts of dry salt are required to effectively release a sufficient quantity of heat to reduce the condensation on the goods or in the wet pack. Larger amounts may be required in actual practice because of heat lost to the environment, other than that directed to the goods. If it is desirable for a particular application to heat the entire package which encloses the goods, more reactant will be required than in those situations where it is only noncorrosive property becomes less important. In gas sterilization, the amount of heat released should be as little as possible to effect condensation reduction, yet avoid damage to heat labile materials. The moisture typically present on goods in a particular process can be readily determined by weight gain measurements. The weight of the pack is measured before and after the process. The quantity of heat needed to evaporate such moisture, or to prevent the formation of condensate in the first place, can be calculated as the product of the mass of moisture collected and the heat of vaporization of water. The effective amount of a particular reactant required to release the determined quantity of heat sufficient to reduce the condensate on the goods, can then be calculated as the quotient of the heat requirement and the "net heat available" for the reactant.

For example, suppose 10 grams of water typically is found condensed in a package of goods. The heat requirement to eliminate that condensate is:

$$M \cdot H = (10 \text{ g}) \cdot (540 \text{ cal/g}) = 5400 \text{ cal}$$

where
M=mass of condensed water;
H=heat of vaporization of water; and
·=multiplication symbol.

Now suppose calcium sulfate is to be used to generate the required heat by taking up two moles of water per mole of CaSO$_4$. The minimum mass of calcium sulfate required to release 5400 cal, assuming complete hydration to two moles of water per mole of CaSO$_4$, is estimated as follows:

$$Mm = \frac{\text{heat needed}}{nha} = \frac{5,400 \text{ cal}}{1014 \text{ cal/g}} = 5.3 \text{ g}$$

where
nha="net heat available" from the reaction as determined from Table III; and
Mm=minimum mass of CaSO$_4$.

Although hydratable salts are preferred for their simplicity and economy, particularly in steam sterilization, other reactants capable of an exothermic reaction which will safely release the desired quantities of heat for the desired purpose will suffice, and in some applications, may be preferred.

What is claimed is:

1. In a process for sterilizing goods in which a quantity of said goods are enclosed in a sterilant-permeable package, and during which process a condensable vapor contacts said goods, an improvement for yielding substantially dry goods at the conclusion of said process comprising:
   providing an exothermic reaction during said process between effective amounts of said condensable vapor and a reactant, said reaction releasing at least a sufficient quantity of heat proximate to said goods to substantially reduce condensate on said goods by the conclusion of said process.

2. The process recited in claim 1 wherein condensate is formed in said package from said condensable vapor during said sterilizing process and said heat is released in such sufficient quantity to reevaporate said condensate.

3. The process recited in claim 1 wherein said heat is released in such sufficient quantity to substantially reduce the formation of condensate within said package from said condensable vapor.

4. The process recited in claim 1 wherein said reactant is a hydratable salt, said salt having a heat of hydration sufficient to release said quantity of heat at a rate that will yield said substantially dry goods at the conclusion of said sterilizing process.

5. The process recited in claim 4 wherein said sterilizing process has a maximum temperature and said hydratable salt has a dehydration temperature greater than said maximum temperature of said process.

6. The process recited in claim 1 wherein the step of producing said exothermic reaction comprises exposing a barrier which separates said vapor from said reactant to a predetermined temperature achieved during a preselected stage of said sterilizing process, said predetermined temperature being sufficient to melt said barrier to expose said vapor to said reactant.

* * * * *